(12) United States Patent
Sahlholm et al.

(10) Patent No.: US 11,147,527 B2
(45) Date of Patent: Oct. 19, 2021

(54) FILLING MICROMECHANICAL STRUCTURES WITH X-RAY ABSORBING MATERIAL

(71) Applicant: SCINT-X AB, Kista (SE)

(72) Inventors: Anna Sahlholm, Huddinge (SE); Olof Svenonius, Stockholm (SE); Daniel Nilsson, Farsta (SE); David Rihtnesberg, Enskededalen (SE)

(73) Assignee: SCINT-X AB, Kista (SE)

(*) Notice: Subject to any disclaimer, the term of this patent is extended or adjusted under 35 U.S.C. 154(b) by 2 days.

(21) Appl. No.: 16/627,483

(22) PCT Filed: Jun. 4, 2018

(86) PCT No.: PCT/SE2018/050569
§ 371 (c)(1),
(2) Date: Dec. 30, 2019

(87) PCT Pub. No.: WO2019/004895
PCT Pub. Date: Jan. 3, 2019

(65) Prior Publication Data
US 2020/0155099 A1    May 21, 2020

Related U.S. Application Data

(60) Provisional application No. 62/527,641, filed on Jun. 30, 2017.

(51) Int. Cl.
*A61B 6/00* (2006.01)
*G01T 1/20* (2006.01)
(52) U.S. Cl.
CPC ............ *A61B 6/484* (2013.01); *A61B 6/4291* (2013.01); *G01T 1/20* (2013.01)

(58) Field of Classification Search
CPC .......... A61B 6/484; A61B 6/4291; G01T 1/20
See application file for complete search history.

(56) References Cited

U.S. PATENT DOCUMENTS

2003/0128812 A1* 7/2003 Appleby ................ B29C 39/34
378/147
2007/0183580 A1 8/2007 Popescu et al.
(Continued)

FOREIGN PATENT DOCUMENTS

CN    102664054        9/2012
CN    102664054 A  *  9/2012
(Continued)

OTHER PUBLICATIONS

Arvay et al., "Characterization techniques for gas diffusion layers for proton exchange membrane fuel cells," Journal of Power Source 213 (2012) 317-337.
(Continued)

*Primary Examiner* — Blake C Riddick
(74) *Attorney, Agent, or Firm* — Nixon & Vanderhye (57) ABSTRACT

There is provided a method and system for filling micromechanical structures with x-ray absorbing material. The method includes providing a wetting layer for enabling melted x-ray absorbing material to flow over the surface of an overall structure including the micromechanical structures, melting the x-ray absorbing material, and applying gas pressure to press the melted x-ray absorbing material into the micromechanical structures.

19 Claims, 5 Drawing Sheets

(56) References Cited

U.S. PATENT DOCUMENTS

| | | | |
|---|---|---|---|
| 2010/0127180 A1* | 5/2010 | Lifshitz | G01T 1/2002 |
| | | | 250/367 |
| 2010/0276829 A1 | 11/2010 | Yang et al. | |
| 2013/0164457 A1* | 6/2013 | Ehlers | G21K 1/06 |
| | | | 427/555 |
| 2014/0138881 A1 | 5/2014 | Chang et al. | |
| 2014/0305904 A1 | 10/2014 | Lan | |
| 2018/0304352 A1* | 10/2018 | Mortensen | C03C 23/0025 |
| 2018/0347070 A1* | 12/2018 | Sahlholm | C30B 11/002 |
| 2019/0004187 A1* | 1/2019 | Sahlholm | G01T 1/20 |

FOREIGN PATENT DOCUMENTS

| | | |
|---|---|---|
| EP | 3179481 | 6/2017 |
| EP | 2 943 808 B1 | 7/2019 |
| WO | 2014/109691 A1 | 7/2014 |

OTHER PUBLICATIONS

Romano et al., "High aspect ration metal microcasing by hot embossing for X-ray optics fabrication," Microelectronic Engineering 176 (2017) 6-10.

International Search Report, PCT/SE2018/050569, dated Aug. 20, 2018.

Extended European Search Report issued in European Patent Application No. 18824828.0 dated Mar. 1, 2021.

\* cited by examiner

FILLING MICROMECHANICAL STRUCTURES WITH X-RAY ABSORBING MATERIAL

TECHNICAL FIELD

The invention generally relates to a method and system for filling micromechanical structures with x-ray absorbing material, as well as a component having such micromechanical structures filled with x-ray absorbing material.

BACKGROUND

In the field of x-ray technology, there is a general need to provide components, such as absorption gratings, scintillators or similar structures having micromechanical structures that are filled with x-ray absorbing or sensitive material.

For example, phase contrast x-ray systems have x-ray absorbing components, where an x-ray absorbing material is deposited in gratings used to create and detect phase shifts.

It is common practice to set up an x-ray imaging system such that an object is placed in the x-ray beam between the x-ray source and the detector. In case of a phase contrast imaging system, it is common practice to also place a number of gratings in the x-ray beam, between the source and the detector. The purpose of these gratings is to create an interference pattern such that when an object is placed in the x-ray beam, its phase-shift and scatter properties affect the interference pattern. The resulting interference pattern can then be read by a detector and, with appropriate algorithms, allows image reconstruction of the object's phase contrast and scatter properties. This apparatus is typically referred to as a grating interferometer. By capturing several images, with slight differences in the relative position of the gratings, three types of images can be captured with such a system: the absorption image ("classic" x-ray image), the phase-contrast image (which represent the refractive properties of an object) and the dark-field image (which represent the scattering properties of an object). In this way, an x-ray examination can provide information that is not attainable with classic absorption x-ray. For example, the phase contrast image can be used to distinguish between different types of liquids or different types of soft tissue; the dark field image can be used to image fine-detail structures such as the alveoli in the lungs.

Figure 2:
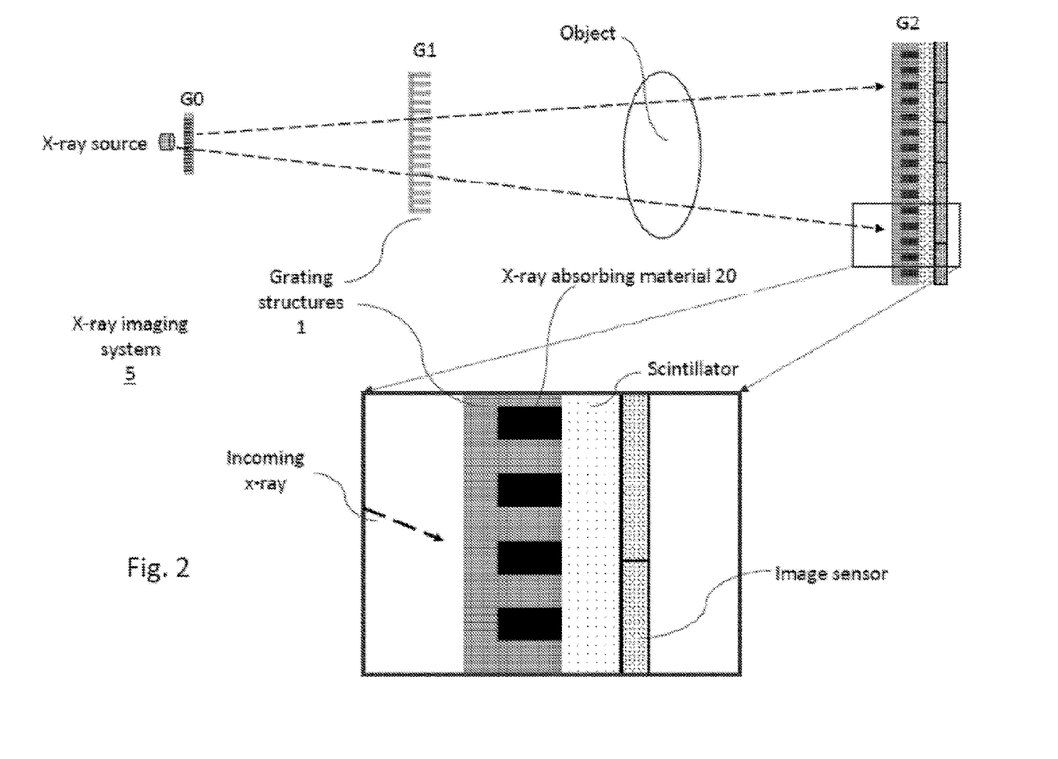
FIG. 2 is an exemplary schematic diagram illustrating an x-ray imaging system such as a phase contrast x-ray system with three gratings.
Figure 3A:
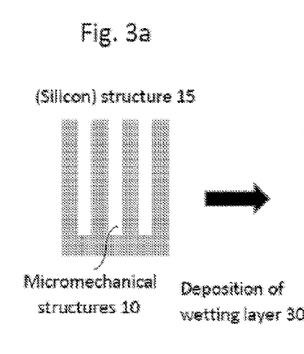
FIG. 3a is a schematic diagram illustrating an example of a grating such as a silicon grating.
Figure 3B:
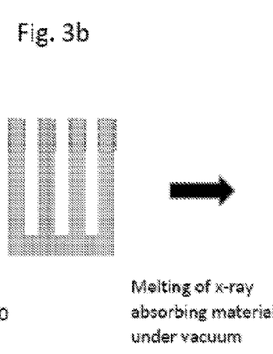
FIG. 3b is a schematic diagram illustrating an example of a grating such as a silicon grating with a wetting layer such as a metal wetting layer.
Figure 3C:
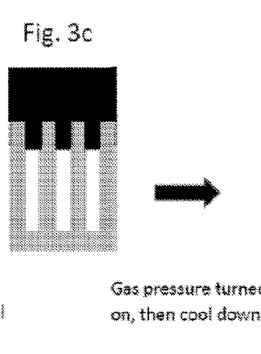
FIG. 3c is a schematic diagram illustrating an example of a grating such as a silicon grating with wetting layer and x-ray absorbing material such as an alloy in vacuum.
Figure 3D:
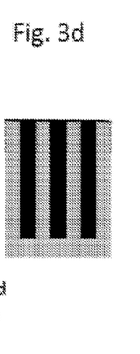
FIG. 3d is a schematic diagram illustrating an example of a grating such as a silicon grating with a wetting layer and x-ray absorbing material such as an alloy in high pressure.

FIG. 2 is a schematic diagram illustrating an exemplary phase contrast x-ray system with three gratings; a source grating G0, a phase grating G1 and an analyzer absorption grating G2.

An example of an x-ray system with such a set of gratings can be found in US2007/0183580, which relates to a focus/detector system of an x-ray apparatus for generating phase contrast recordings. The system includes a beam source with a focus, equipped with a focus-side source grating G0, arranged in the beam path generating a field of ray-wise coherent x-rays, a grating/detector arrangement having a phase grating G1 and grating lines arranged parallel to the source grating for generating an interference pattern, an analyzer grating G2 and a detector having a multiplicity of detector elements arranged flat for measuring the position-dependent radiation intensity behind the phase grating.

In initial research work, the fill material of choice has been gold; however, because a substantial amount of gold is required to fill a whole grating, and because gold is a very expensive material, this solution is not commercially viable for widespread use. Current research indicates that other materials may also be possible to use.

Research has also suggested approaches using mechanical pressure to force material into the micromechanical structures, but these solutions are not easily scalable to high volume production with large structures.

There is thus a general need for improvements regarding the process of filling micromechanical structures with x-ray absorbing material.

SUMMARY

The present invention overcomes these and other drawbacks of the prior art.

It is an object to provide an improved component, such as an absorption grating, scintillator or similar structure having micromechanical structures filled with x-ray absorbing or sensitive material, with respect to manufacturability, scalability, and cost.

It is also an object to provide a fast melting/solidification process, which enables a short cycle time in production.

It is a specific object to provide a method for filling micromechanical and possibly porous structures with x-ray absorbing material.

It is another specific object to provide a system for filling micromechanical and possibly porous structures with x-ray absorbing material.

As an example, for the specific application of manufacturing absorption gratings, x-ray absorbing materials are traditionally chosen among the heavy elements. The inventors have found that also some lighter materials can be good x-ray absorbers in a specific energy range.

The proposed technology may be regarded as a method for manufacturing a component, such as an absorption grating, scintillator or similar structure, having micromechanical structures to be filled with x-ray absorbing material.

In particular, it is desirable to have a component, such as an absorption grating, scintillator, or similar structure, having micromechanical structures, where the micromechanical structures are filled with a suitable x-ray absorbing material, using methods and processes scalable to production volumes.

For example, the inventors have realized that it is possible to use gas pressure to force melted x-ray absorbing material into the micromechanical structures. This is facilitated and/or enabled by a wetting layer which allows the melted x-ray absorbing material to flow over the entire surface of the overall structure, creating a lid which makes it possible to press, by gas pressure, the material into the micromechanical structures.

The application of the wetting layer can thus be regarded as a surface modification to allow for efficient pressurized filling of the micromechanical structures with melted x-ray absorbing material.

By way of example, the x-ray absorbing material may be selected as a material suitable for filling grating lines of an absorption grating or provided as a suitable scintillating material for a scintillator.

According to a first aspect, there is thus provided a method for filling micromechanical structures with x-ray absorbing material, wherein the method comprises at least the following basic process steps: providing a wetting layer for enabling melted x-ray absorbing material to flow over the surface of an overall structure comprising the micromechanical structures, melting the x-ray absorbing material and applying gas pressure to press the melted x-ray absorbing material into the micromechanical structures.

According to a second aspect, there is provided a method for manufacturing a component having micromechanical structures to be filled with x-ray absorbing material, comprising the method according to the first aspect.

According to a third aspect, there is provided a component such as an absorption grating or scintillator manufactured using the method according to the first aspect.

According to a fourth aspect, there is provided an x-ray imaging system comprising such a component.

According to a fifth aspect, there is provided a corresponding system for filling micromechanical structures with x-ray absorbing material. By way of example, there is provided a system for filling micromechanical structures with x-ray absorbing material, wherein the system is configured for enabling application of a wetting layer over at least part of the surface of an overall structure comprising the micromechanical features to allow melted x-ray absorbing material to flow over the surface of the overall structure, wherein the system is configured for melting the x-ray absorbing material; and wherein the system is configured for applying gas pressure to press the melted x-ray absorbing material into the micromechanical structures.

The micromechanical structures may include any deep, narrow structures such as pores, trenches or any geometry which combines pores and trenches. By way of example, the micromechanical structures may be part of a grating structure or even a structured scintillator.

Basically, the invention offers one or more of the following advantages: Better manufacturability, better scalability to large size gratings and lower cost.

The invention is particularly useful in the following technical applications: Phase contrast and dark field imaging, primarily for use in medical examinations but also suitable for security, non-destructive testing and scientific applications.

Other advantages of the invention will be appreciated when reading the below detailed description.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The invention will now be described with reference to some exemplary and non-limiting embodiments.

Figures 1A, 1B:
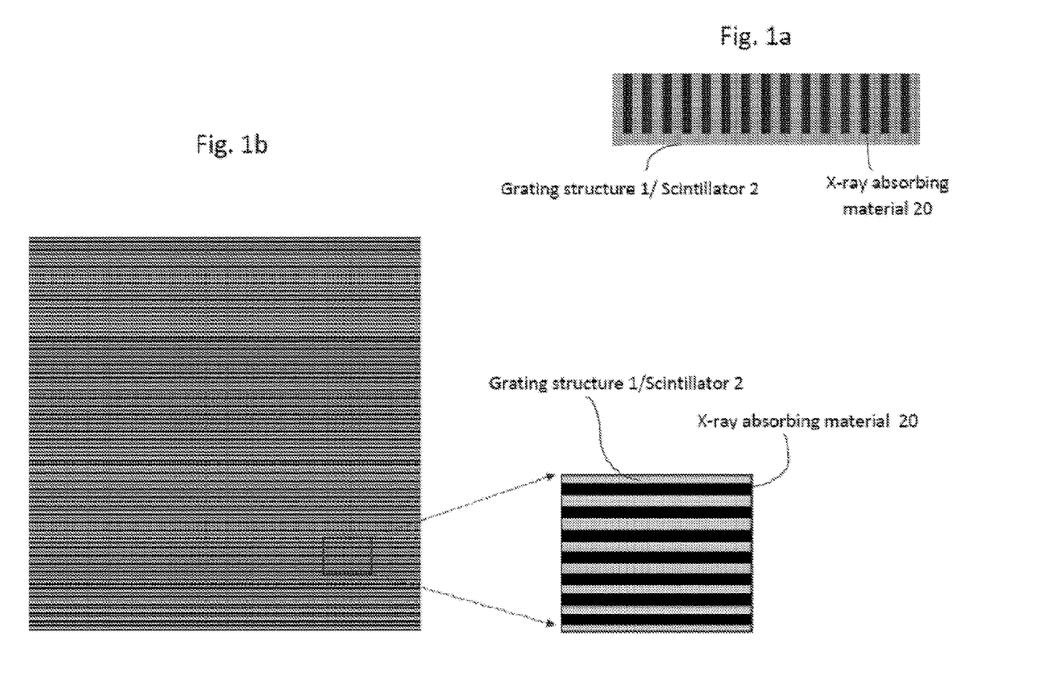
FIG. 1a is schematic diagram illustrating an example of a grating structure or scintillator seen from the side, where the grating is basically a structure with long trenches separated by dividing walls.
FIG. 1b is a schematic diagram illustrating an example of a grating structure or scintillator seen from above.

FIG. 1a is schematic diagram illustrating an example of a grating structure 1 or scintillator 2 seen from the side. In this example, the grating structure 1 is basically a structure with long trenches separated by dividing walls.

FIG. 1b is a schematic diagram illustrating an example of a grating structure 1 or scintillator 2 seen from above.

FIG. 2 is an exemplary schematic diagram illustrating an x-ray imaging system 5 such as a phase contrast x-ray system with three gratings, also referred to as grating structures 1; a source grating G0, a phase grating G1 and an analyzer absorption grating G2. The G0 and G2 gratings are absorption gratings, which means that they are filled with x-ray absorbing material 20, whereas the G1 grating is a phase grating without fill material. The source grating (G0), typically placed close to the X-ray tube, is an aperture mask with transmitting slits. It creates an array of periodically repeating line sources and effectively enables the use of relatively large, X-ray sources, without compromising the coherence requirements of the arrangement formed by G1 and G2. The image contrast itself is formed via the combined effect of the two gratings G1 and G2. The second grating (G1) acts as a phase mask, and imprints periodic phase modulations onto the incoming wave field. Through the Talbot effect, the phase modulation is transformed into an intensity modulation in the plane of G2, forming a linear periodic interference pattern perpendicular to the optical axis and parallel to the lines of G1. The third grating (G2), with absorbing lines and the same periodicity and orientation as the interference pattern created by G1, is placed in the detection plane, immediately in front of the detector. When one of the gratings is scanned along the transverse direction, the intensity signal in each pixel detector plane oscillates, which can be read out by the detector.

FIG. 3a-d shows an example of a grating 1 such as a silicon grating during the different stages of the filling process starting from an overall structure such as a silicon structure having micromechanical structures 10 such as pores and/or trenches, coating with wetting layer 30, distribution of x-ray absorbing material 20, and filling through gas pressure. The micromechanical structures 10 are defined in the overall structure 15.

Figure 4A:
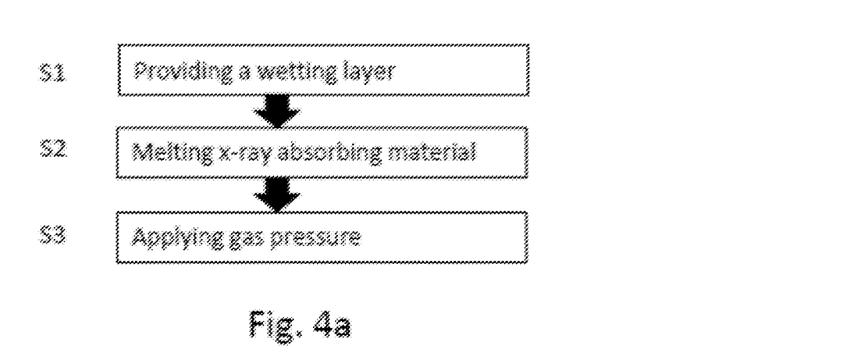
FIG. 4a is a schematic diagram illustrating an example of a method for filling micromechanical structures with x-ray absorbing material according to an embodiment.

FIG. 4a is a schematic diagram illustrating an example of a method for filling micromechanical structures with x-ray absorbing material according to an embodiment.

Basically, the method for filling micromechanical structures with x-ray absorbing material comprises the following basic process steps:

providing (S1) a wetting layer for enabling melted x-ray absorbing material to flow over the surface of the overall structure or component, melting (S2) the x-ray absorbing material over the surface; and applying (S3) gas pressure to press the melted x-ray absorbing material into the micromechanical structures.

In other words, a wetting layer 30 may be applied over at least part of the surface of an overall structure 15 comprising micromechanical features or structures 10 to be filled by an x-ray absorbing material 20. Subsequently, the x-ray absorbing material is melted over the micromechanical structures. The wetting layer allows the melted x-ray absorbing material to flow over the overall surface and optionally/possibly partly into the micromechanical structures, thus effectively creating a lid that facilitates the process of pressing the material into the micromechanical structures by gas pressure.

The proposed technology may alternatively be seen as a method for manufacturing a component, such as an absorption grating or scintillator, having micromechanical structures to be filled with x-ray absorbing material.

For example, the application of the wetting layer may be regarded as a surface modification to allow for efficient pressurized filling of the micromechanical structures with melted x-ray absorbing material.

As mentioned, the micromechanical structures may be part of a grating structure or a structured scintillator. By way of example, the micromechanical structures include pores, trenches, recessions or any geometry which combines pores and trenches and/or recessions defined in an overall physical structure 15.

In a particular example, the overall structure is an overall silicon structure comprising the micromechanical structures 10, and the step S1 of providing a wetting layer 30 comprises depositing the wetting layer on the surface and possibly some tens of micrometers into the micromechanical structures 10 of the overall silicon structure 15 to provide a coated surface.

For example, the method may take place in a vacuum/pressure cabinet in which the overall silicon structure 15 is placed in connection with a temperature-controlled heater. The x-ray absorbing material 20 is distributed on the coated surface of the overall silicon structure 15, and vacuum is pumped in the cabinet. The temperature may then be raised to enable melting of the x-ray absorbing material (20), and the temperature is preferably maintained while the melt flows over the surface and at least partly into the micromechanical structures. Gas pressure may then be turned on in the cabinet to press the melted x-ray absorbing material 20 into the micromechanical structures 10 until the micromechanical features are filled with x-ray absorbing material.

Preferably, the temperature in the cabinet is ramped down to room temperature to enable solidification of the x-ray absorbing material inside the micromechanical structures.

As an example, the x-ray absorbing material 20 may include one or more elements or materials having their K-edges below, or in the lower end, of the intended x-ray spectrum.

For example, the intended x-ray spectrum may be in the 30-90 keV range, and the x-ray absorbing material 20 may be selected among materials, which have their characteristic absorption K-edges at or below 30 keV.

By way of example, the x-ray absorbing material may include silver, indium and/or tin.

As an example, the wetting layer 30 may include a non-oxidizing metal.

For example, the wetting layer 30 may include gold, copper, iridium and/or platinum.

By way of example, the inventors have recognized that indium is a particularly advantageous choice of x-ray absorbing material, due to its unique combination of good x-ray absorption properties, suitable melting point, low toxicity, optimal viscosity and low relative cost. In particular, indium is an excellent choice as x-ray absorbing material in combination with gold as material for the wetting layer, e.g., because (when melted) indium flows very well on a gold wetting layer. In this way, the melted indium can flow out very easily over the surface of the overall structure.

In a particular example, the x-ray absorbing material thus includes indium and the wetting layer includes gold.

Figure 4B:
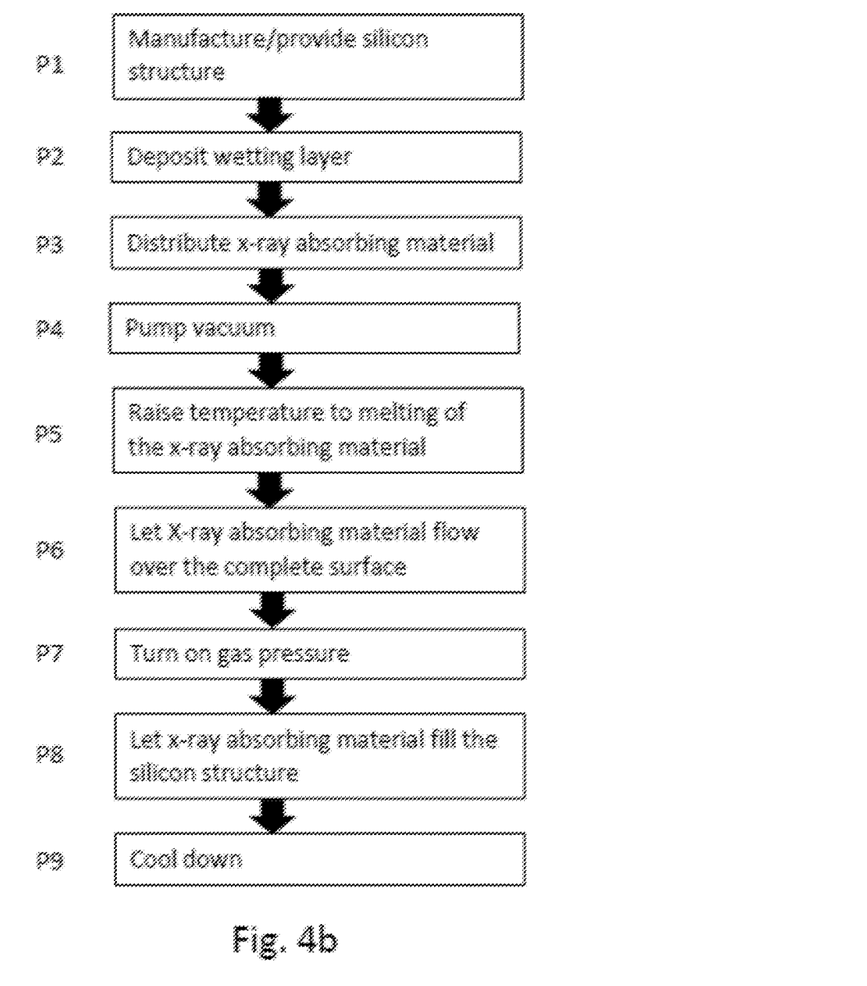
FIG. 4b is an exemplary flow diagram illustrating a non-limiting example of a typical melting/solidification process comprising a number of phases.

FIG. 4*b* is an exemplary flow diagram illustrating a non-limiting example of a typical melting/filling/solidification process comprising a number of phases.

An exemplary x-ray absorbing alloy has a melting temperature of approximately 200° C. Other x-ray absorbing materials with melting points below the melting temperature of the micromechanical structure may also be used. In a particular example, a micromechanical structure of silicon can be used, which has a melting temperature of about 1410° C.

In this particular example, there are one or more of the following phases:

Phase 1: Manufacture and/or provide a silicon structure tuned for the given application.

Phase 2: Deposit a wetting layer on the surface and possibly some tens of micrometers into the micromechanical structures/features of the overall silicon structure.

Phase 3: Distribute the x-ray absorbing material on the surface of the silicon structure with wetting layer.

Phase 4: Pump vacuum.

Phase 5: Raise the temperature to enable melting of the x-ray absorbing material.

Phase 6: Wait (i.e. maintain the set temperature) while the melt flows over the surface and at least partly into the micromechanical structures.

Phase 7: Turn on the gas pressure.

Phase 8: Wait until the x-ray absorbing material has filled the voids in the silicon structure. In other words, wait until the micromechanical features are filled to a suitable degree.

Phase 9: Ramp down entire system to room temperature to enable solidification of the x-ray absorbing material inside the micromechanical structures. This concludes the process cycle.

Phase 1 and 2 can be done separately from the subsequent phases. Standard equipment for silicon processing can be used for performing selected process steps during the above phases.

Any suitable x-ray absorbing material may be used. However, the inventors have realized that some relatively light materials, which are not typically considered good x-ray absorbers because of their relatively low atomic number and density, may in fact also be quite good x-ray absorbers in the 30-90 keV range typically used in medical examinations. These may for example be relatively light materials, which have their characteristic absorption K-edges at or below 30 keV.

For example, it is an advantage if the x-ray absorbing material is suitable for filling into a silicon structure, which enables the use of efficient silicon wafer-processing methods. In addition, the selected material should preferably be suitable for filling in the micromechanical structures by melting.

By way of example, suitable materials may include elements or materials having their K-edges below, or in the lower end, of the intended x-ray spectrum, or alloys or mixtures thereof or alloys or mixtures comprising any of these elements. Examples include elements from period 5, such as silver, indium and tin, having their K-edges below, or in the lower end, of the intended x-ray spectrum. In addition, the materials preferably have low toxicity and are solid at room temperature.

It is important that the material for the wetting layer is chosen to suit the intended x-ray absorbing material. As an example, some materials from period 5 of the periodic table have quite good x-ray absorption properties in the 30-90 keV range and would be suitable for a large number of applications. Examples include silver, indium and tin, as described above. These materials wet well on a non-oxidizing metal such as gold, copper, iridium, and platinum.

From a practical point of view, it is also important that in phase 6 there are no or only insignificant uncovered parts of the surface, as that will let gas leak into the silicon structure, creating pressure from the inside, and prevent the x-ray absorbing material from filling the void underneath.

For the manufacturing of a scintillator, any suitable scintillating material can be used. For example, caesium iodide (CsI), which has a melting temperature of approximately 620° C., may be used. Other scintillating materials with melting points below the melting temperature of the micromechanical structure may also be used.

According to a complementary aspect, there is provided a system for filling micromechanical structures with x-ray absorbing material. The system is configured for enabling application of a wetting layer over at least part of the surface of an overall structure comprising the micromechanical features to allow melted x-ray absorbing material to flow over the surface of the overall structure. The system is also configured for melting the x-ray absorbing material, and configured for applying gas pressure to press the melted x-ray absorbing material into the micromechanical structures.

Figure 5:
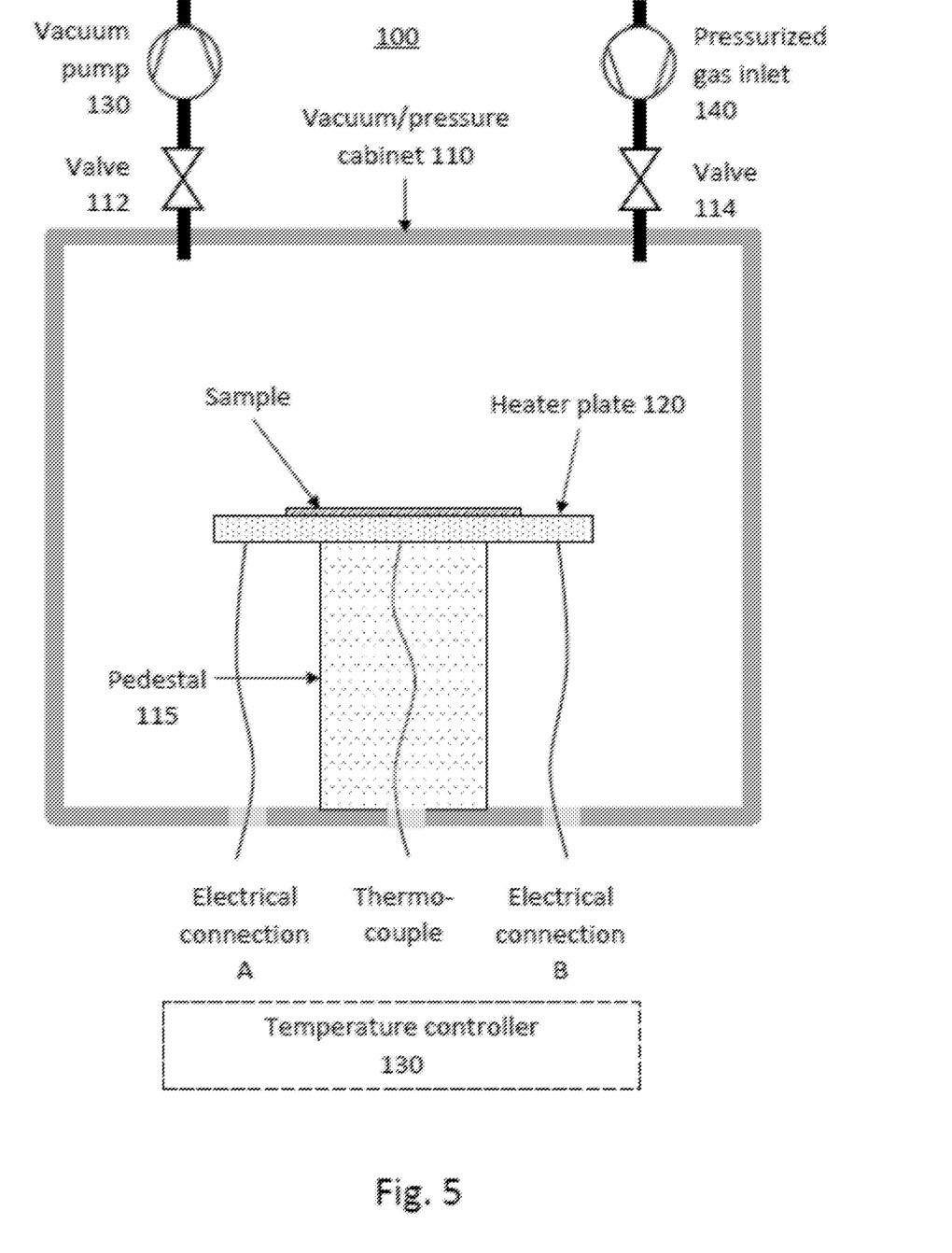
FIG. 5 is a schematic diagram illustrating an example of a melting/solidification system seen from the side.

FIG. 5 is a schematic diagram illustrating an example of a melting/solidification system seen from the side. In this example, the system 100 comprises a vacuum/pressure cabinet 110, and a heater 120 placed inside the cabinet, wherein the heater is regulated by a temperature controller 130, and the vacuum/pressure cabinet 110 has two valves 112, 114, one for a vacuum pump 130 and one for a pressurized gas inlet 140.

For example, the system 100 comprises a heater plate 120, e.g. placed on a pedestal 115 inside the vacuum/pressure cabinet 110. The heater 120 may be regulated by a temperature controller 130, receiving input from one or more thermocouples placed in physical contact with the heater 120. As mentioned above, the vacuum and/or pressure cabinet 110 may have two valves 112; 114, one for a vacuum pump 130 and one for a pressurized gas inlet 140.

The system may be configured for melting and solidification of x-ray absorbing material in micromechanical structures, in the manner as described herein.

By way of example, the time duration of each relevant phase (4-9) is typically determined by programmed parameters in the temperature controllers, such as temperature ramp speeds in ° C. per minute and hold times in minutes. It is also determined by the pressure in Bar, which can be controlled separately or by the same system that controls the temperature. The thermal time constant of the system and available power available to the heaters may limit the speed with which temperature can be raised or lowered. In this exemplary melting/solidification system, the time duration for phases 4-9 combined is typically less than one hour.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. A method for filling micromechanical structures with x-ray absorbing material, the method comprising:
   providing a wetting layer configured to enable melted x-ray absorbing material to flow over a surface of an overall structure comprising the micromechanical structures, the providing the wetting layer comprising applying the wetting layer over at least part of the surface of the overall structure, thereby providing coating with the wetting layer;
   distributing and melting the x-ray absorbing material over the coated surface; and
   applying gas pressure to press the melted x-ray absorbing material into the micromechanical structures,
   wherein the wetting layer allows the melted x-ray absorbing material to flow over the overall structure and partway into the micromechanical structures, thus effectively creating a lid that facilitates the pressing of the melted x-ray absorbing material into the micromechanical structures by the gas pressure.

2. The method of claim 1, wherein the applying of the wetting layer is a surface modification to allow for efficient pressurized filling of the micromechanical structures with the melted x-ray absorbing material.

3. The method of claim 1, wherein the micromechanical structures are part of a grating structure or a structured scintillator.

4. The method of claim 1, wherein the micromechanical structures include pores, trenches, recessions or any geometry which combines one or more of pores, trenches and recessions defined in the overall structure.

5. The method of claim 1, wherein the overall structure is an overall silicon structure comprising the micromechanical structures, and the providing of the wetting layer comprises depositing the wetting layer on the surface and up to tens of micrometers into the micromechanical structures of the overall silicon structure to provide a coated surface.

6. The method of claim 2, wherein the method takes place in a vacuum/pressure cabinet in which the overall silicon structure is placed in connection with a temperature-controlled heater,
   the method further comprising
      distributing the x-ray absorbing material on the coated surface of the overall silicon structure, and pumping a vacuum in the cabinet,
      raising a temperature to enable melting of the x-ray absorbing material, and maintaining the temperature while the melted x-ray absorbing material flows over the surface and at least partway into the micromechanical structures, and
      turning gas pressure on in the vacuum/pressure cabinet to press the melted x-ray absorbing material into the micromechanical structures until the micromechanical features are filled with the x-ray absorbing material.

7. The method of claim 6, further comprising ramping the temperature in the cabinet down to room temperature to enable solidification of the x-ray absorbing material inside the micromechanical structures.

8. The method of claim 1, wherein the x-ray absorbing material includes one or more elements or materials having K-edges below, or in the lower end, of an intended x-ray spectrum.

9. The method of claim 8, wherein the intended x-ray spectrum is in the 30-90 keV range, and the x-ray absorbing material is selected among materials having characteristic absorption K-edges at or below 30 keV.

10. The method of claim 1, wherein the x-ray absorbing material includes one or more of silver, indium, and tin.

11. The method of claim 1, wherein the wetting layer includes one or more of gold, copper, iridium, and platinum.

12. The method of claim 1, wherein the x-ray absorbing material includes indium, and the wetting layer includes gold.

13. A method for manufacturing a component having micromechanical structures to be filled with x-ray absorbing material, the method comprising the method of claim 1.

14. A component manufactured using the method according to claim 13.

15. The component of claim 14, wherein the component is an absorption grating or scintillator.

16. An x-ray imaging system comprising:
the component of claim 14.

17. A system for filling micromechanical structures with x-ray absorbing material,
wherein the system is configured to
enable application of a wetting layer over at least part of a surface of an overall structure comprising the micromechanical structures to thereby provide coating with the wetting layer and allow melted x-ray absorbing material to flow over the surface of the overall structure,
distribute and melt the x-ray absorbing material over the coated surface,
apply gas pressure to press the melted x-ray absorbing material into the micromechanical structures, and
enable, by applying the wetting layer, the melted x-ray absorbing material to flow over the overall structure and partway into the micromechanical structures, thus effectively creating a lid that facilitates the pressing of the melted x-ray absorbing material into the micromechanical structures by the gas pressure.

18. The system of claim 17, further comprising:
a vacuum/pressure cabinet having two valves, one of the valves being for a vacuum pump, the other of the valves being for a pressurized gas inlet; and
a heater disposed inside the vacuum/pressure cabinet, the heater being regulated by a temperature controller.

19. The system of claim 17, wherein the system is configured to melt and solidify the x-ray absorbing material in the micromechanical structures.

* * * * *